(12) United States Patent
Nordstrom et al.

(10) Patent No.: US 6,385,484 B2
(45) Date of Patent: May 7, 2002

(54) SPECTROSCOPIC SYSTEM EMPLOYING A PLURALITY OF DATA TYPES

(75) Inventors: Robert J. Nordstrom, Hanover; Peter J. Costa, Hudson; Kwong Hui, Woburn; Ross Flewelling, Chelmsford; Howard Kaufman, Newton, all of MA (US)

(73) Assignee: MediSpectra, Inc., Lexington, MA (US)

( * ) Notice: Subject to any disclaimer, the term of this patent is extended or adjusted under 35 U.S.C. 154(b) by 0 days.

(21) Appl. No.: 09/738,613

(22) Filed: Dec. 15, 2000

Related U.S. Application Data

(63) Continuation-in-part of application No. 09/470,071, filed on Dec. 22, 1999.
(60) Provisional application No. 60/113,761, filed on Dec. 23, 1998.

(51) Int. Cl.$^7$ .................................................. A61B 6/00
(52) U.S. Cl. ...................... 600/476; 600/473; 600/478; 356/301
(58) Field of Search .............................. 600/310, 473, 600/476, 478

(56) References Cited

U.S. PATENT DOCUMENTS

| | | | |
|---|---|---|---|
| 3,013,467 A | 12/1961 | Minsky | 88/14 |
| 3,809,072 A | 5/1974 | Ersek et al. | 128/23 |
| 4,017,192 A | 4/1977 | Rosenthal et al. | 356/201 |
| 4,198,571 A | 4/1980 | Sheppard | 250/571 |

(List continued on next page.)

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |
| EP | 0 474 264 | 3/1992 |
| EP | 0 641 542 | 3/1995 |
| EP | 0 689 045 A1 | 12/1995 |
| SU | 1 223 092 | 4/1986 |
| WO | WO 93/14688 | 8/1993 |
| WO | WO 94/26168 | 11/1994 |
| WO | WO 95/04385 | 2/1995 |
| WO | WO 97/05473 | 2/1997 |
| WO | WO 98/30889 | 2/1997 |
| WO | WO 98/41176 | 9/1998 |

OTHER PUBLICATIONS

P. Davidovits et al. "Scanning Laser Microscope for Biological Investigations", Applied Optics, vol. 10, No. 7, pp. 1615–1619, Jul. 1971.

C.J.R. Sheppard et al. " Depth of Field in the Scanning Microscope", Optics Letters, vol. 3, No. 3, Sep. 1978, pp. 115–117.

C.J. Koester, "Scanning Mirror Microscope with Optical Sectioning Characteristics: Applications in Ophthalmology", Applied Optics. vol. 19, No. 11, Jun. 1980, pp. 1749–1757.

(List continued on next page.)

Primary Examiner—Marvin M. Lateef
Assistant Examiner—Runa Shah Qaderi
(74) Attorney, Agent, or Firm—Testa, Hurwitz & Thibeault, LLP

(57) ABSTRACT

A system and method for classifying specimens using a plurality of spectral data types. Spectra are recorded as amplitudes at a series of discrete wavelengths. Pluralities of reference spectra are recorded for specimens having known conditions. A spectrum of a first type is observed for a test specimen. The specimen is characterized as to a first known condition. In the event that the specimen does not exhibit the first known condition, a spectrum of a second type is observed and analyzed to determine which of a plurality of conditions is to be ascribed to the test specimen. In some embodiments, the test specimen can comprise human cervical tissue, and the known conditions can include normal health, metaplasia, CIN I and CIN II/II.

23 Claims, 7 Drawing Sheets

U.S. PATENT DOCUMENTS

| | | | |
|---|---|---|---|
| 4,254,421 A | 3/1981 | Kreutel, Jr. | 343/754 |
| 4,357,075 A | 11/1982 | Hunter | 350/294 |
| 4,397,557 A | 8/1983 | Herwig et al. | 356/342 |
| 4,662,360 A | 5/1987 | O'Hara et al. | 128/9 |
| 4,733,063 A | 3/1988 | Kimura et al. | 250/201 |
| 4,741,326 A | 5/1988 | Sidall et al. | 128/4 |
| 4,753,530 A | 6/1988 | Knight et al. | 356/73 |
| 4,768,513 A | 9/1988 | Suzuki | 128/634 |
| 4,844,617 A | 7/1989 | Kelderman et al. | 356/372 |
| 4,845,352 A | 7/1989 | Benschop | 250/201 |
| 4,852,955 A | 8/1989 | Doyle et al. | 350/1.2 |
| 4,877,033 A | 10/1989 | Seitz, Jr. | 128/660.05 |
| 4,878,485 A | 11/1989 | Adair | 128/6 |
| 4,891,829 A | 1/1990 | Deckman et al. | 378/4 |
| 4,930,516 A | 6/1990 | Alfano et al. | 128/665 |
| 4,945,478 A | 7/1990 | Merickel et al. | 364/413.22 |
| 4,965,441 A | 10/1990 | Picard | 250/201.3 |
| 4,972,258 A | 11/1990 | Wolf et al. | 358/93 |
| 4,974,580 A | 12/1990 | Anapliotis | 128/4 |
| 4,979,498 A | 12/1990 | Oneda et al. | 128/6 |
| 4,997,242 A | 3/1991 | Amos | 350/6.91 |
| 5,003,979 A | 4/1991 | Merickel et al. | 364/413.22 |
| 5,011,243 A | 4/1991 | Doyle et al. | 350/1.2 |
| 5,022,757 A | 6/1991 | Modell | 356/318 |
| 5,028,802 A | 7/1991 | Webb et al. | 250/571 |
| 5,032,720 A | 7/1991 | White | 250/236 |
| 5,034,613 A | 7/1991 | Denk et al. | 250/458.1 |
| 5,036,853 A | 8/1991 | Jeffcoat et al. | 128/634 |
| 5,042,494 A | 8/1991 | Alfano | 128/665 |
| 5,054,926 A | 10/1991 | Dabbs et al. | 356/345 |
| 5,065,008 A | 11/1991 | Hakamata et al. | 250/216 |
| 5,071,246 A | 12/1991 | Blaha et al. | 351/221 |
| 5,074,306 A | 12/1991 | Green et al. | 128/664 |
| 5,083,220 A | 1/1992 | Hill | 359/234 |
| 5,091,652 A | 2/1992 | Mathies et al. | 250/458.1 |
| 5,120,953 A | 6/1992 | Harris | 250/227.2 |
| 5,122,653 A | 6/1992 | Ohki | 250/216 |
| 5,132,526 A | 7/1992 | Iwasaki | 250/201.3 |
| 5,139,025 A | 8/1992 | Lewis et al. | 128/665 |
| 5,154,166 A | 10/1992 | Chikama | 128/4 |
| 5,159,919 A | 11/1992 | Chikama | 128/4 |
| 5,161,053 A | 11/1992 | Dabbs | 359/384 |
| 5,162,641 A | 11/1992 | Fountain | 250/201.2 |
| 5,162,941 A | 11/1992 | Favro et al. | 359/386 |
| 5,168,157 A | 12/1992 | Kimura | 250/234 |
| 5,192,980 A | 3/1993 | Dixon et al. | 356/326 |
| RE34,214 E | 4/1993 | Carlsson et al. | 358/93 |
| 5,201,318 A | 4/1993 | Rava et al. | 128/665 |
| 5,201,908 A | 4/1993 | Jones | 128/4 |
| 5,225,671 A | 7/1993 | Fukuyama | 250/216 |
| 5,235,457 A | 8/1993 | Lichtman et al. | 359/368 |
| 5,237,984 A | 8/1993 | Williams, III et al. | 128/4 |
| 5,239,178 A | 8/1993 | Derndinger et al. | 250/234 |
| 5,248,876 A | 9/1993 | Kerstens et al. | 250/561 |
| 5,257,617 A | 11/1993 | Takahashi | 128/4 |
| 5,260,569 A | 11/1993 | Kimura | 250/234 |
| 5,260,578 A | 11/1993 | Bliton et al. | 250/461.1 |
| 5,261,410 A | 11/1993 | Alfano et al. | 128/664 |
| 5,262,646 A | 11/1993 | Booker et al. | 250/341 |
| 5,274,240 A | 12/1993 | Mathies et al. | 250/458.1 |
| 5,284,149 A | 2/1994 | Dhadwal et al. | 128/665 |
| 5,286,964 A | 2/1994 | Fountain | 250/201.2 |
| 5,294,799 A | 3/1994 | Aslund et al. | 250/458.1 |
| 5,296,700 A | 3/1994 | Kumagai | 250/216 |
| 5,303,026 A * | 4/1994 | Strobl et al. | 356/318 |
| 5,306,902 A | 4/1994 | Goodman | 250/201.3 |
| 5,313,567 A | 5/1994 | Civanlar et al. | 395/124 |
| 5,319,200 A | 6/1994 | Rosenthal et al. | 250/341 |
| 5,321,501 A | 6/1994 | Swanson et al. | 356/345 |
| 5,324,979 A | 6/1994 | Rosenthal | 250/504 R |
| 5,325,846 A | 7/1994 | Szabo | 128/4 |
| 5,329,352 A | 7/1994 | Jacobsen | 356/301 |
| 5,337,734 A | 8/1994 | Saab | 128/4 |
| 5,343,038 A | 8/1994 | Nishiwaki et al. | 250/234 |
| 5,345,306 A | 9/1994 | Ichimura et al. | 356/346 |
| 5,398,685 A | 3/1995 | Wilk et al. | 128/653.1 |
| 5,402,768 A | 4/1995 | Adair | 128/4 |
| 5,406,939 A | 4/1995 | Bala | 128/4 |
| 5,413,092 A | 5/1995 | Williams, III et al. | 128/4 |
| 5,413,108 A | 5/1995 | Alfano | 128/665 |
| 5,415,157 A | 5/1995 | Welcome | 128/4 |
| 5,418,797 A | 5/1995 | Bashkansky et al. | 372/3 |
| 5,419,311 A | 5/1995 | Yabe et al. | 128/4 |
| 5,421,337 A | 6/1995 | Richards-Kortum et al. | 128/665 |
| 5,421,339 A | 6/1995 | Ramanujam et al. | 128/665 |
| 5,451,931 A | 9/1995 | Muller et al. | 340/630 |
| 5,458,132 A | 10/1995 | Yabe et al. | 128/4 |
| 5,458,133 A | 10/1995 | Yabe et al. | 600/121 |
| 5,477,382 A | 12/1995 | Pernick | 359/559 |
| 5,480,775 A | 1/1996 | Ito et al. | 435/7.2 |
| 5,493,444 A | 2/1996 | Khoury et al. | 359/559 |
| 5,507,295 A | 4/1996 | Skidmore | 600/121 |
| 5,516,010 A | 5/1996 | O'Hara et al. | 600/122 |
| 5,529,235 A | 6/1996 | Bolarski et al. | 227/175.1 |
| 5,536,236 A | 7/1996 | Yabe et al. | 600/125 |
| 5,545,121 A | 8/1996 | Yabe et al. | 600/121 |
| 5,551,945 A | 9/1996 | Yabe et al. | 600/122 |
| 5,556,367 A | 9/1996 | Yabe et al. | 600/124 |
| 5,587,832 A | 12/1996 | Krause | 359/385 |
| 5,596,992 A | 1/1997 | Haaland et al. | 128/664 |
| 5,609,560 A | 3/1997 | Ichikawa et al. | 600/101 |
| 5,623,932 A | 4/1997 | Ramanujam et al. | 128/665 |
| 5,662,588 A | 9/1997 | Lida | 600/121 |
| 5,685,822 A | 11/1997 | Harhen | 600/125 |
| 5,693,043 A | 12/1997 | Kittrell et al. | 606/15 |
| 5,695,448 A | 12/1997 | Kimura et al. | 600/121 |
| 5,697,373 A * | 12/1997 | Richards-Kortum | 600/475 |
| 5,704,892 A | 1/1998 | Adair | 600/121 |
| 5,707,343 A | 1/1998 | O'Hara et al. | 600/121 |
| 5,713,364 A | 2/1998 | DeBaryshe et al. | 128/664 |
| 5,730,701 A | 3/1998 | Furukawa et al. | 600/127 |
| 5,733,244 A | 3/1998 | Yasui et al. | 600/127 |
| 5,746,695 A | 5/1998 | Yasui et al. | 600/127 |
| 5,768,333 A | 6/1998 | Abdel-Mottaleb | 378/37 |
| 5,769,792 A | 6/1998 | Palcic et al. | 600/477 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,813,987 A | 9/1998 | Modell et al. | 600/473 |
| 5,817,015 A | 10/1998 | Adair | 600/121 |
| 5,833,617 A | 11/1998 | Hayashi | 600/476 |
| 5,855,551 A | 1/1999 | Sklandnev et al. | 600/372 |
| 5,860,913 A | 1/1999 | Yamaya et al. | 600/127 |
| 5,865,726 A | 2/1999 | Katsurada et al. | 600/127 |
| 5,876,329 A | 3/1999 | Harhen | 600/125 |
| 5,931,779 A * | 8/1999 | Arakaki et al. | 600/310 |
| 6,091,985 A * | 7/2000 | Alfano et al. | 600/476 |
| 6,095,982 A * | 8/2000 | Richards-Kortum | 600/476 |
| 6,104,945 A | 8/2000 | Modell et al. | 600/473 |
| 6,119,031 A | 9/2000 | Crowley | 600/407 |
| 6,146,897 A * | 11/2000 | Cohenford et al. | 436/63 |
| 6,169,817 B1 | 1/2001 | Parker et al. | 382/131 |

OTHER PUBLICATIONS

T. Wilson., "The Role of the Pinhold in Confocal Imaging Systems", Confocal Microscopy Handbook, pp. 99–113.

C. Koester, "Comparison of Optical Sectioning Methods: The Scanning Slit Confocal Microscope", Confocal Microscope Handbook, pp. 189–194.

Jeffrey W. Hall, et al. "Near–Infrared Spectrophotometry: A New Dimension in Clinical Chemistry", Clin. Chem 38/9, 1623–1631 (1992).

Kevin T. Schomacker, et al. "Ultraviolet Laser–Induced Fluorescence of Colonic Tissue; Basic Biology and Diagnostic Potential", Lasers in Surgery and Medicine, 12: 63–78, (1992).

S. Schwartz, "Real–time laser–scanning Confocal ratio imaging", American Laboratory, pp. 53–62 Apr. 1993.

R. Richards–Kortum et al. Description and Performance of a Fiber–optic Confocal Fluorescence Spectrometer, Applied Spectroscopy, vol. 48, No. 3, pp. 350–355. (1994).

J.M. Schmitt et al. "Interferometric Versus Confocal Techniques for Imaging Microstructures in Turbid Biological Media", Proc. SPIE, 2135 (1994), pp. 1–12.

N. Ramanujam et al. Fluorescence Spectroscopy; A Diagnostic Tool for Cervical Intraepithelial Neoplasia (CIN), Gynecologic Oncology 52, pp. 31–38 (1994).

S.G. Anderson, "Confocal Laser Microscopes See A Wider Field of Application", Laser Focus World, pp. 83–86, Feb. 1994.

J.M. Schmitt et al. "Confocal Microscopy in Turbid Media", J. Opt. Soc. Am., vol. II, pp. 2225–2235, Aug. 1994.

N. Ramanujam et al. "In vivo diagnosis of cervical intraepithelial neoplasia using 337–nm–exited laser–induced fluorescence", Pro. Natl. Acad. Sci. USA, vol. 91, pp. 10193–10197, Oct. 1994.

* cited by examiner

SPECTROSCOPIC SYSTEM EMPLOYING A PLURALITY OF DATA TYPES

CROSS-REFERENCE TO RELATED APPLICATIONS

This application is a continuation-in-part of U.S. patent application Ser. No. 09/470,071, filed Dec. 22, 1999, which claims priority to and the benefit of U.S. provisional patent application Ser. No. 60/113,761, filed Dec. 23, 1998, and this application is related to the U.S. patent application entitled, "System for Normalizing Spectra" and identified by Ser. No. 09/738,612, filed on even date herewith, and to the U.S. patent application entitled, "Spectral Data Classification Of Samples" and identified by Ser. No. 09/738,481, filed on even date herewith. All of the above applications are assigned to the common assignee of this application, and are hereby incorporated by reference.

GOVERNMENT RIGHTS

This invention was made with government support under Contract No. CA 66481 awarded by National Cancer Institute, NIH. The government may have certain rights in the invention.

FIELD OF THE INVENTION

This invention relates generally to spectroscopic systems. More particularly, in one embodiment, the invention relates to a spectroscopic system for characterizing test specimens using a plurality of spectral data types.

BACKGROUND OF THE INVENTION

Spectral analysis of biological specimens has been used for disease diagnosis. In general, spectra are recorded as values of amplitude, typically measured as a response to an excitation, as a function of wavelength (or the inverse of wavelength, namely frequency). In the field of spectral analysis, different kinds of information are conveyed by different spectral types. For example, fluorescence spectra are recorded using a source of excitation illumination that is absorbed by a specimen and that causes the specimen to emit a fluorescence spectrum that depends in part on the transfer of energy within and among atoms and/or molecules in the specimen. An illumination source for use in observing and recording fluorescence spectra generally operates at a selected monochromatic wavelength, or a narrow range of wavelengths. Different sources of illumination that operate at different wavelengths can excite different constituents of a specimen. In addition, different sources of illumination that operate at different wavelengths can excite the same constituent with different efficiencies. Thus, a fluorescence spectrum can depend on both the excitation wavelength that is used to illuminate a specimen and on the composition of the specimen itself. Other effects also play a role in determining a fluorescence spectrum, for example, instrumental effects, effects relating to polarization of the illumination, or thermal effects.

Some progress has been made in using various optical spectral methods for analysis of test specimens, including biological specimens. However, the wide variety of physical and chemical influences present in a test specimen that play roles in determining an observed spectrum make difficult both the choice of a suitable illumination source, and the interpretation of the resulting spectrum. This is in part true because there are so many influences on the kind and amount of information that an optical spectrum conveys that it is hard to find clear cause and effect relationships among the multitude of competing influences.

SUMMARY OF THE INVENTION

The invention provides methods of determining the disease state of a biological specimen based upon a reflectance spectrum residual derived by subtracting from a reflectance spectrum obtained from a test specimen an average reflectance spectrum obtained from a plurality if healthy specimens. In a preferred embodiment, members of the plurality of healthy specimens are determined to be healthy based upon the fluorescence spectra emitted by those samples. Typically, the specimen to be tested exhibits a fluorescence spectrum that is not characteristic of healthy tissue.

The reflectance spectrum residual provides a criterion for diagnostic classification of a specimen that is judged to be indeterminate in classification by its fluorescence spectrum alone. Accordingly, methods of the invention resolve diagnostic ambiguities created when a specimen produces a fluorescence spectrum that is not characteristic of a healthy tissue. Similarly, methods of the invention are also useful to resolve diagnostic ambiguities created when the fluorescence spectrum of a test specimen is not characteristic of any known disease state.

In one aspect, the invention provides a method of determining a condition of a test specimen. The method comprises recording both fluorescence and reflectance spectra from specific specimen. The method then comprises identifying a plurality of specimens having a fluorescence spectrum characteristic of a known condition; obtaining an average reflectance spectrum based upon the plurality of first test specimens; obtaining a reflectance spectrum from a test specimen that produces a fluorescence spectrum that is not characteristic of the known condition; and obtaining a reflectance spectrum residual by subtracting the average reflectance spectrum from the reflectance spectrum obtained from the test specimen. Determination of the condition of the test specimen is based upon the reflectance spectrum residual. In a preferred embodiment, the condition of the test specimen is based upon an amplitude of one or more features of the reflectance spectrum residual. For purposes of the invention a "condition" is a state of disease, including a healthy state or simply the physiological makeup of the specimen and/or the patient from whom it was obtained.

In one embodiment, the plurality of specimens producing the average reflectance spectrum comprises tissue specimens and the test specimen is a tissue specimen of the same type. In one embodiment, the tissue specimens are human cervical tissue specimens, the condition of which is healthy, and the condition of the test specimen is determined by methods of the invention. In one embodiment, cervical tissue producing the average reflectance spectrum are selected from normal squamous tissue, metaplasia, mile cervical intraepithelial neoplasia (CIN I), and moderate to severe cervical intraepithelial neoplasia (CIN II/III). In another embodiment, methods of the invention further comprise obtaining additional optical information from the test specimen, and evaluating the additional optical information in comparison to the fluorescence spectrum and the reflectance spectrum from the test specimen to determine the condition of the test specimen. In one embodiment, the additional optical information is video information. In another embodiment, the additional optical information is an optical image.

In one aspect, the invention relates to a spectroscopic system for determining a condition of a test specimen. The system comprises a data collection module that collects a fluorescence spectrum characteristic of a known condition from each of a plurality of first specimens, observes a reflectance spectrum from each member of the plurality, and observes a reflectance spectrum from a test specimen that is observed to produce a second fluorescence spectrum that is not characteristic of the known condition. The system further comprises a computation module that computes an average reflectance spectrum based upon each member of the plurality of first specimens, and that computes a reflectance spectrum residual by subtracting the average reflectance spectrum from the reflectance spectrum obtained from a test specimen, and an analysis module that determines the condition of the test specimen based at least in part upon the reflectance spectrum residual.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

The invention relates to the use of multiple types of spectral data for determining the status of a test specimen. In the present invention, a first spectral observation is used to distinguish between a first condition and a plurality of other conditions, and a second observation using information obtained from a different type of spectral data is used to distinguish among the plurality of other conditions. The invention will be described in terms of embodiments that relate to the use of multiple optical spectra in characterization systems and methods, particularly in the area of medical diagnostics, and especially as such use relates to the analysis of spectra obtained from human cervical tissue in the detection of cervical cancer. However, the invention has applicability generally in the area of characterization of test specimens based on analysis of a plurality of optical spectra types.

Figure 1:
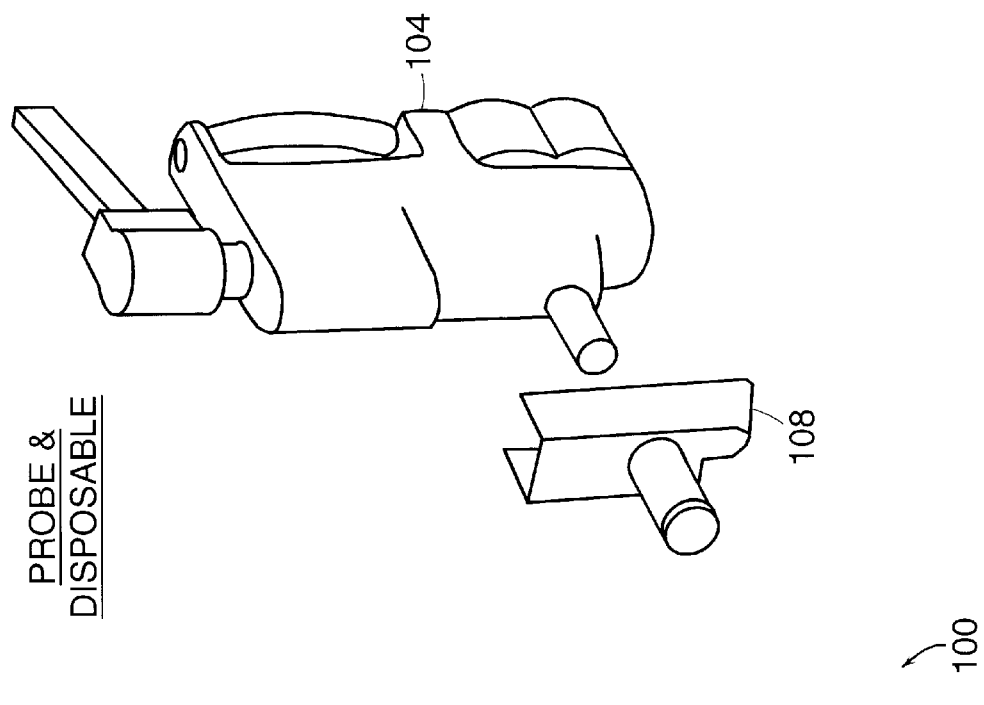
FIG. 1 shows an exemplary spectroscopic system that employs a plurality of spectral types according to an illustrative embodiment of the invention.
Figure 1:
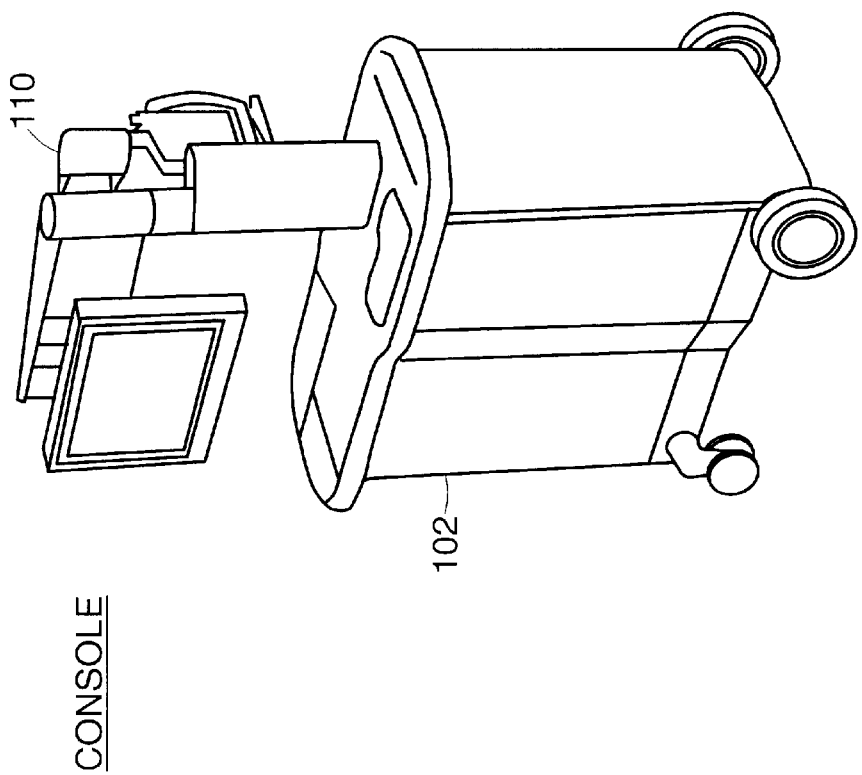

FIG. 1 depicts an exemplary spectroscopic system 100 employing a plurality of spectral data types in methods and systems according to an illustrative embodiment of the invention. The spectroscopic system includes a console 102 connected to a probe 104 by a cable 106. The cable 106 carries electrical and optical signals between the console 102 and the probe 104. The probe 104 accommodates a disposable component 108 which used only once, and discarded after such use. The console 102 and the probe 104 are mechanically connected by an articulating arm 11 0, which can also support the cable 106. The console 102 contains much of the hardware and the software of the system, and the probe 104 contains the necessary hardware for making suitable spectroscopic observations. The details of the system are further explained in conjunction with FIG. 2.

Figure 2:
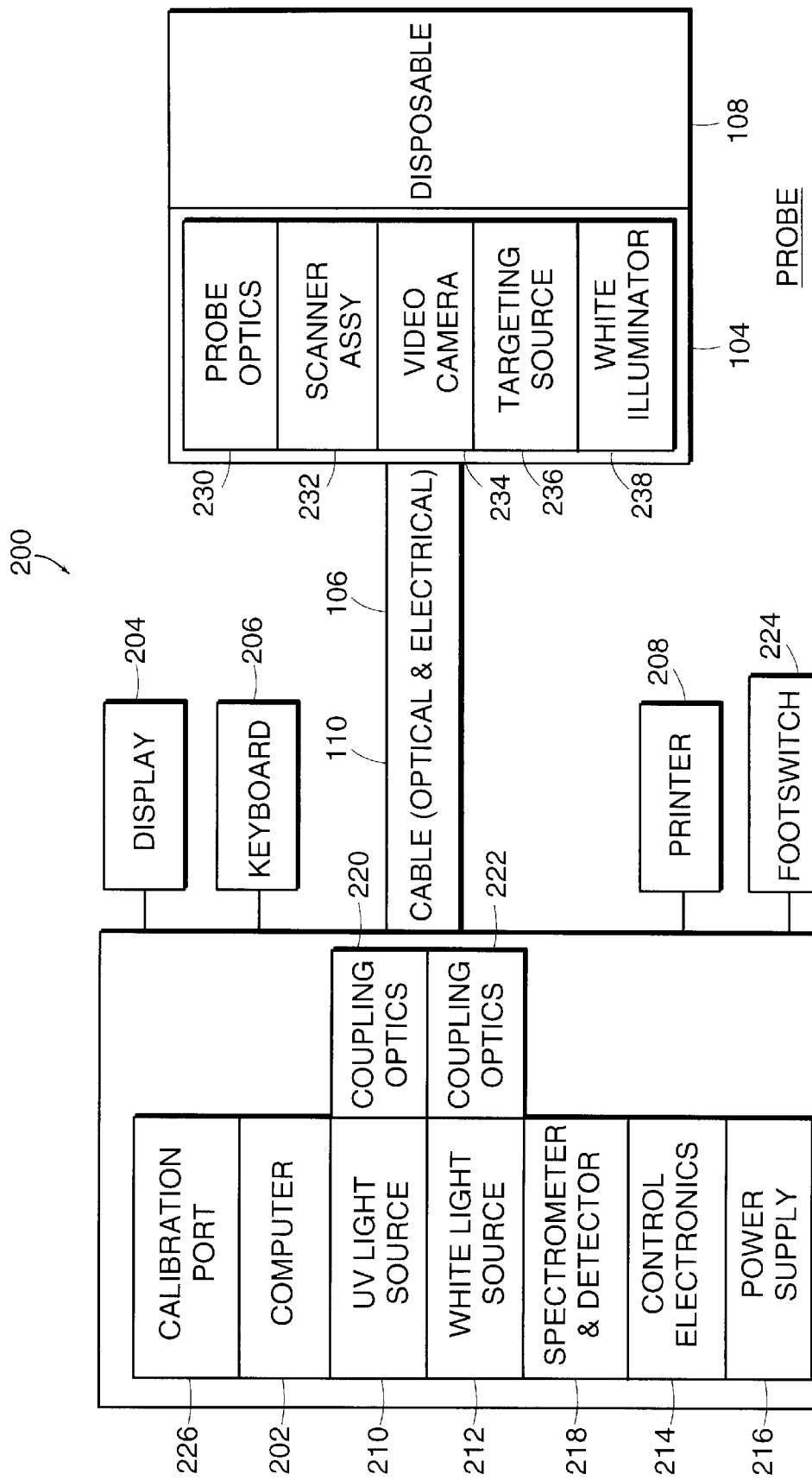
FIG. 2 shows an exemplary operational block diagram of the spectroscopic system of FIG. 1.

FIG. 2 shows an exemplary operational block diagram 200 of a spectroscopic system of the type depicted in FIG. 1. According to an illustrative embodiment, the spectroscopic system of FIGS. 1 and 2 is subtantially the same as single-beam spectrometer devices, but is adapted to include the features of the invention. The console 102 includes a computer 202 which executes software that controls the operation of the spectroscopic system 100. The software includes one or more modules recorded on machine-readable media, which can be any medium such as magnetic disks, magnetic tape, CD-ROM, semiconductor memory, or the like. Preferably, the machine-readable medium is resident within the computer 202. In alternative embodiments, the machine-readable medium can be connected to the computer 202 by a communication link. In alternative embodiments, one can substitute computer insructions in the form of hardwired logic for software, or one can substitute firmware (i.e., computer instructions recorded on devices such as PROMs, EPROMS oe EEPROMs, or the like) for software. The term machine-readable instructions as used herein is intended to encompass software, hardwired logic, firmware and the like.

The computer 202 is a general purpose computer. The computer 202 can be an embedded computer, or a personal computer such as a laptop or desktop computer, that is capable of running the software, issuing suitable control commands, and recording information in real time. The computer 202 has a display 204 for reporting information to an operator of the spectroscopic system 100, a keyboard 206 for enabling the operator to enter information and commands, and a printer 208 for providing a print-out, or permanent record, of measurements made by the spectroscopic system 100 and for printing diagnostic results, for example, for inclusion in the chart of a patient. As described below in more detail, in an illustrative embodiment of the invention, some commands entered at the keyboard, enable a user to select a particular spectrum for analysis or to reject a spectrum, and to select particular segments of a spectrum for normalization. Other commands enable a user to select the wavelength range for each particular segment and to specify both wavelength contiguous and non-contiguous segments.

The console 102 also includes an ultraviolet (UV) source 210 such as a nitrogen laser or a frequency-tripled Nd:YAG laser, a white light source 212 such as one or more Xenon flash lamps, and control electronics 214 for controlling the light sources both as to intensity and as to the time of onset of operation and the duration of operation. One or more power supplies 216 are included in the console 102, to provide regulated power for the operation of all of the components. The console 102 also includes at least one spectrometer and at least one detector (spectrometer and detector 218) suitable for use with each of the light sources. In some embodiments, a single spectrometer can operate with both the UV light source and the white light source. In some embodiments, the same detector can record UV and white light signals, and in some embodiments different detectors are used for each light source.

The console 102 also includes coupling optics 220 to couple the UV illumination from the UV light source 210 to one or more optical fibers in the cable 106 for transmission to the probe 104, and for coupling the white light illumination from the white light source 212 to one or more optical fibers in the cable 106 for transmission to the probe 104. The console 102 also includes coupling optics 222 to couple the spectral response of a specimen to UV illumination from the UV light source 210 observed by the probe 104 and carried by one or more optical fibers in the cable 106 for transmission to the spectrometer and detector 218, and for coupling the spectral response of a specimen to the white light illumination from the white light source 212 observed by the probe 104 and carried by one or more optical fibers in the cable 106 for transmission to the spectrometer and detector 218. The console 102 includes a footswitch 224 to enable an operator of the spectroscopic system 100 to signal when it is appropriate to commence a spectral observation by stepping on the switch. In this manner, the operator has his or her hands free to perform other tasks, for example, aligning the probe 104.

The console 102 includes a calibration port 226 for calibrating the optical components of the spectrometer system. The operator places the probe 104 in registry with the calibration port 226 and issues a command that starts the calibration operation. In the calibration operation, a calibrated light source provides illumination of known intensity as a function of wavelength as a calibration signal. The probe 104 detects the calibration signal. The probe 104 transmits the detected signal through the optical fiber in the cable 106, through the coupling optics 222 to the spectrometer and detector 218. A test spectral result is obtained. A calibration of the spectral system is computed as the ratio of the amplitude of the known illumination at a particular wavelength divided by the test spectral result at the same wavelength.

The probe 104 includes probe optics 230 for illuminating a specimen to be analyzed with UV and white light from the UV source 210 and the white light source 212, and for collecting the fluorescent and backscatter (or reflectance) illumination from the specimen that is being analyzed. The probe includes a scanner assembly 232 that provides illumination from the UV source 210 in a raster pattern over a target area of the specimen of cervical tissue to be analyzed. The probe includes a video camera 234 for observing and recording visual images of the specimen under analysis. The probe 104 includes a targeting souce 236, which can be used to determine where on the surface of the specimen to be analyzed the probe 104 is pointing. The probe 104 also includes a white light illuminator 238 to assist the operator in visualizing the specimen to be analyzed. Once the operator aligns the spectroscopic system and depresses the footswitch 224, the computer 202 controls the actions of the light sources 210, 212, the coupling optics 220, the transmission of light signals and electrical signals through the cable 106, the operation of the probe optics 230 and the scanner assembly 232, the retreival of observed spectra via the cable 106, the coupling of the observed spectra via the coupling optics 222 into the spectrometer and detector 218, the operation of the spectrometer and detector 218, and the subsequent signal procesing and analysis of the recorded spectra.

Figure 3:
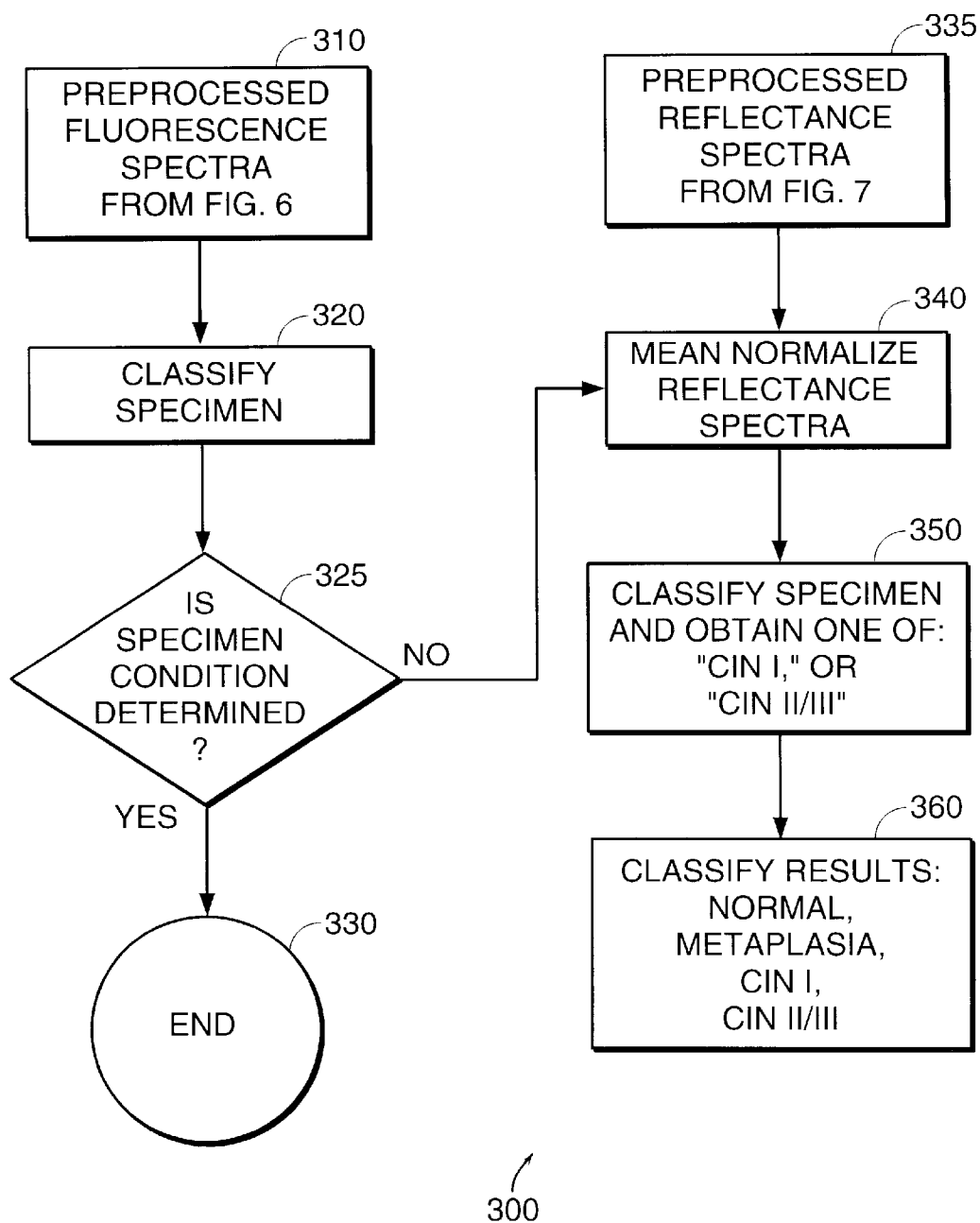
FIG. 3 is a detailed schematic flow diagram showing exemplary steps of combining a fluorescence spectrum analysis described more fully in FIG. 6 with a reflectance spectrum analysis described more fully in FIG. 7 to perform tissue characterization according to an illustrative embodiment of the invention.

FIG. 3 is a detailed schematic flow diagram 300 showing exemplary steps of combining the fluorescence spectrum analysis described more fully in FIG. 6 below with the reflectance spectrum analysis described more fully in FIG. 7 below to perform tissue characterization according to an illustrative embodiment of the invention. Step 310 indicates that the results presented in FIG. 6 for analysis of fluorescence spectra from a test specimen of unknown condition or unknown state of health are available. At step 320, the computer 202 determines whether the test specimen can be classified as "normal," or "metaplasia," or can not be classified by fluorescence spectroscopy alone. This process is described in detail at step 665 of FIG. 6 below. As indicated in step 325, a decision is taken as to whether the test specimen has a definitive state of health, for example that the specimen is "normal." If the test specimen can be classified, for example as normal, the method ends at step 330.

In the event that a definitive condition or state of health cannot be ascribed to a test specimen, the computer 202 further analyses information available from a reflectance spectrum or from a plurality of reflectance spectra taken from the test specimen. At step 335, the computer 202 provides reflectance spectra processed according to the systems and methods described in connection with FIG. 7 below.

If the specimen cannot be classified, a mean normalization step is performed by computer 202, as indicated at step 340. This mean normalization step is described in detail at step 755 of FIG. 7 below. The mean normalization is carried out using a plurality of reflectance spectra taken from specimens that are known to represent normal squamous tissue. In one embodiment, a single test specimen is examined at multiple locations, each location measuring approximately one millimeter in diameter. If one or more locations of the test specimen provide fluorescence spectra that indicate that those locations can be classified as representing normal squamous tissue, using the methods and systems described in FIG. 6 below, the reflectance spectra recorded from those locations are used to mean normalize the reflectance spectra obtained from locations that are not capable of being classified as "normal" or "metaplasia" solely on the basis of fluorescence spectra.

As indicated in step 350, the computer 202 can carry out an analysis using a metric as described in detail at FIG. 7, step 760 below, for example using the Mahalanobis distance as a metric in N-dimensional space. In one embodiment, the test reflectance spectra are truncated to the wavelength regions 391 nm to 484 nm, and 532 nm to 625 nm. In one embodiment, the classifications CIN I and CIN II/II are the classifications that are possible for a test spectrum that is neither classified as "normal" nor "metaplasia" by fluorescence spectral analysis. As indicated at step 350, the computer 202 classifies the test specimen as having a condition or state of health selected from CIN I and CIN II/III based on the value of the metric computed by the computer 202, provided that the value of the metric does not exceed a pre-determined maximum value.

At step 360, the computer 202 presents the results of the classification of the test specimen, as a condition or state of health corresponding to one of normal, metaplasia, CIN I and CIN II/III.

Figure 4:
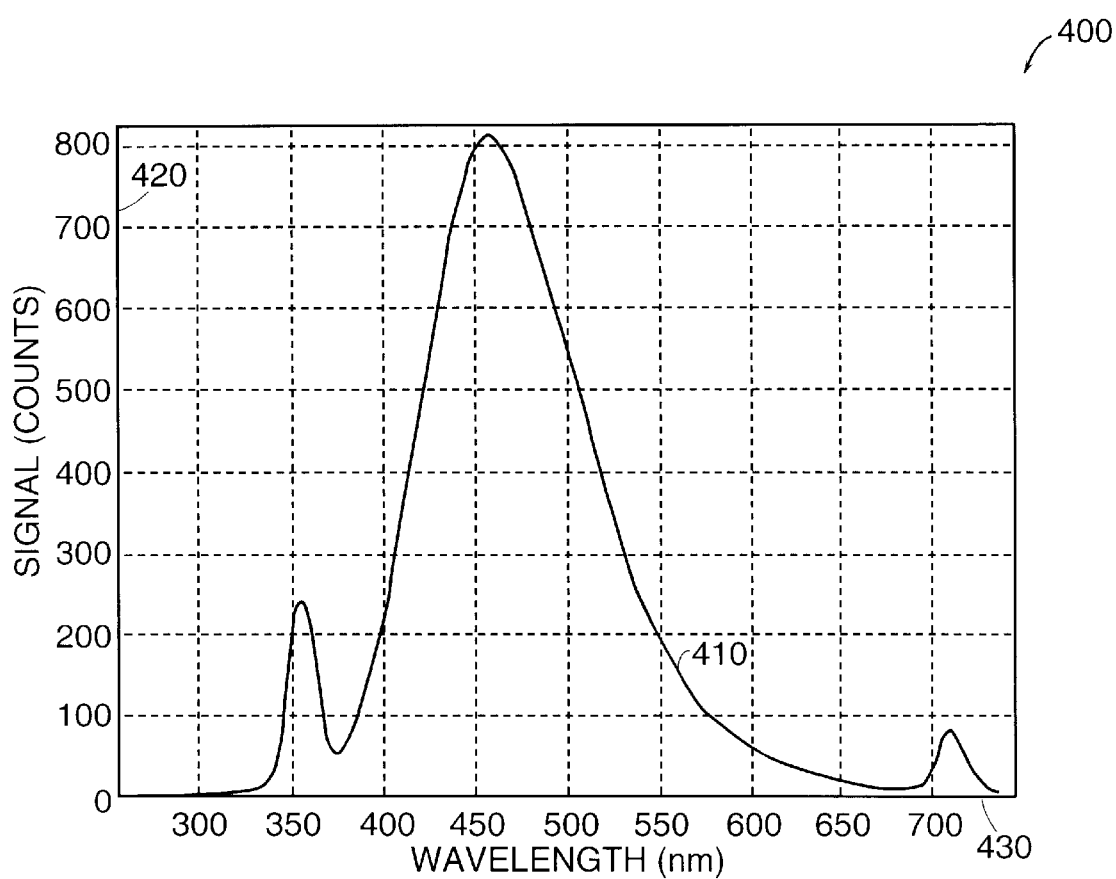
FIG. 4 is a diagram showing an exemplary fluorescence spectrum recorded using the spectroscopic system of FIG. 1.

FIG. 4 is a diagram 400 showing an exemplary fluorescence spectrum recorded using the spectroscopic system of FIG. 1. In FIG. 4, a curve 410 having an amplitude defined in terms of number of counts, for example a signal strength expressed as numbers of photons, as indicated along the vertical axis 420. An amplitude is plotted against a wavelength of light expressed in nm, as indicated along the horizontal axis 430. Such spectra can be recorded using the methods and systems described in FIGS. 1–3 with an illumination source that provides optical excitation comprising a substantially monochromatic source in the ultraviolet portion of the optical spectrum. The exemplary fluorescence spectrum depicted in FIG. 4 was recorded from human cervical tissue using ultraviolet illumination.

Figure 5:
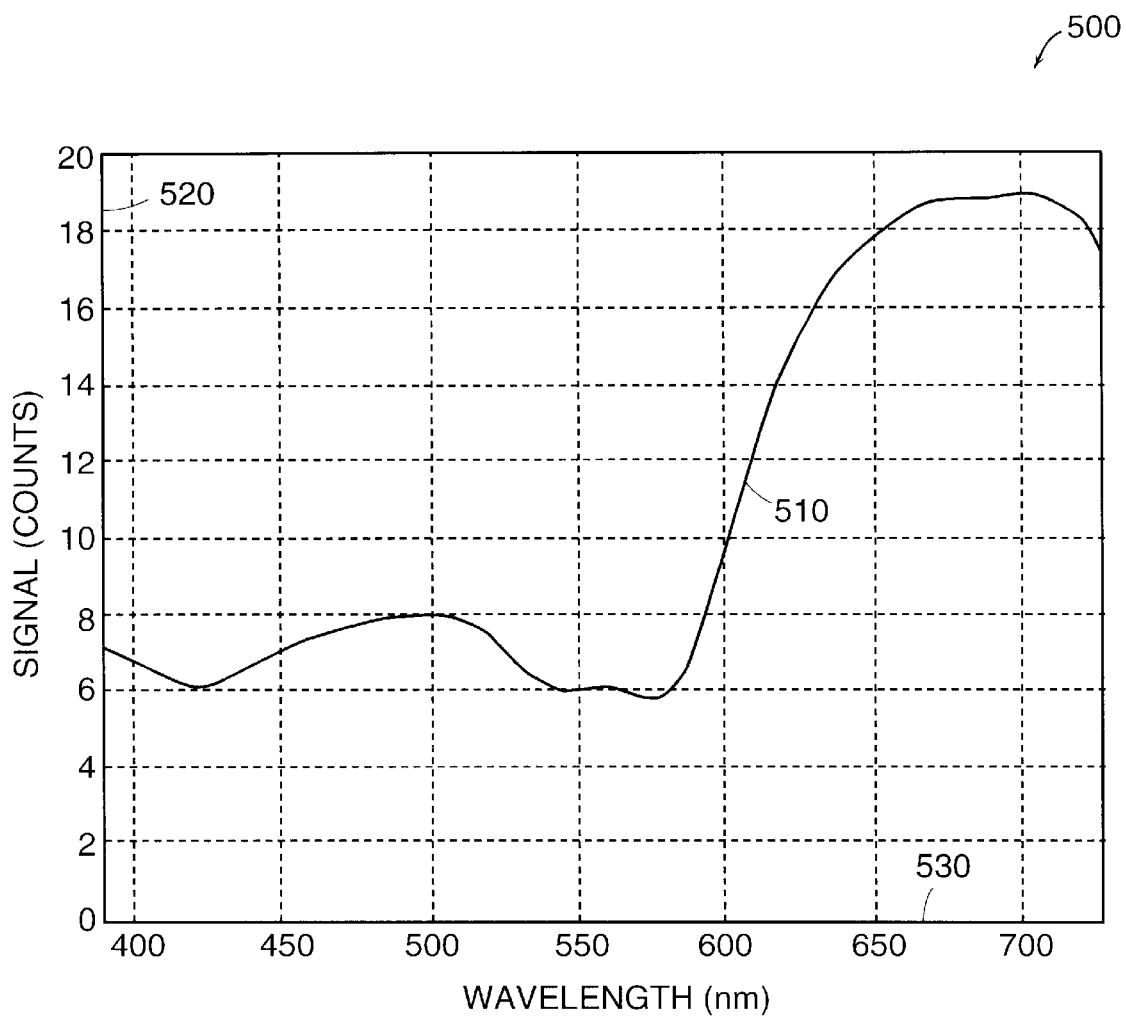
FIG. 5 is a diagram showing an exemplary reflectance spectrum recorded using the spectroscopic system of FIG. 1.

FIG. 5 is a diagram 500 showing an exemplary reflectance spectrum recorded using the spectroscopic system of FIG. 1. In FIG. 5, a curve 510 having an amplitude defined in terms of number of counts, for example a signal strength expressed as numbers of photons, as indicated along the vertical axis 520. An amplitude is plotted against a wavelength of light expressed in nm, as indicated along the horizontal axis 530. Such spectra can be recorded using the methods and systems described in FIGS. 1–3 with an illumination source that provides optical excitation comprising a broadband source in the visible portion of the optical spectrum. The exemplary reflectance spectrum depicted in FIG. 5 was recorded from human cervical tissue using broadband visible light illumination.

Figure 6:
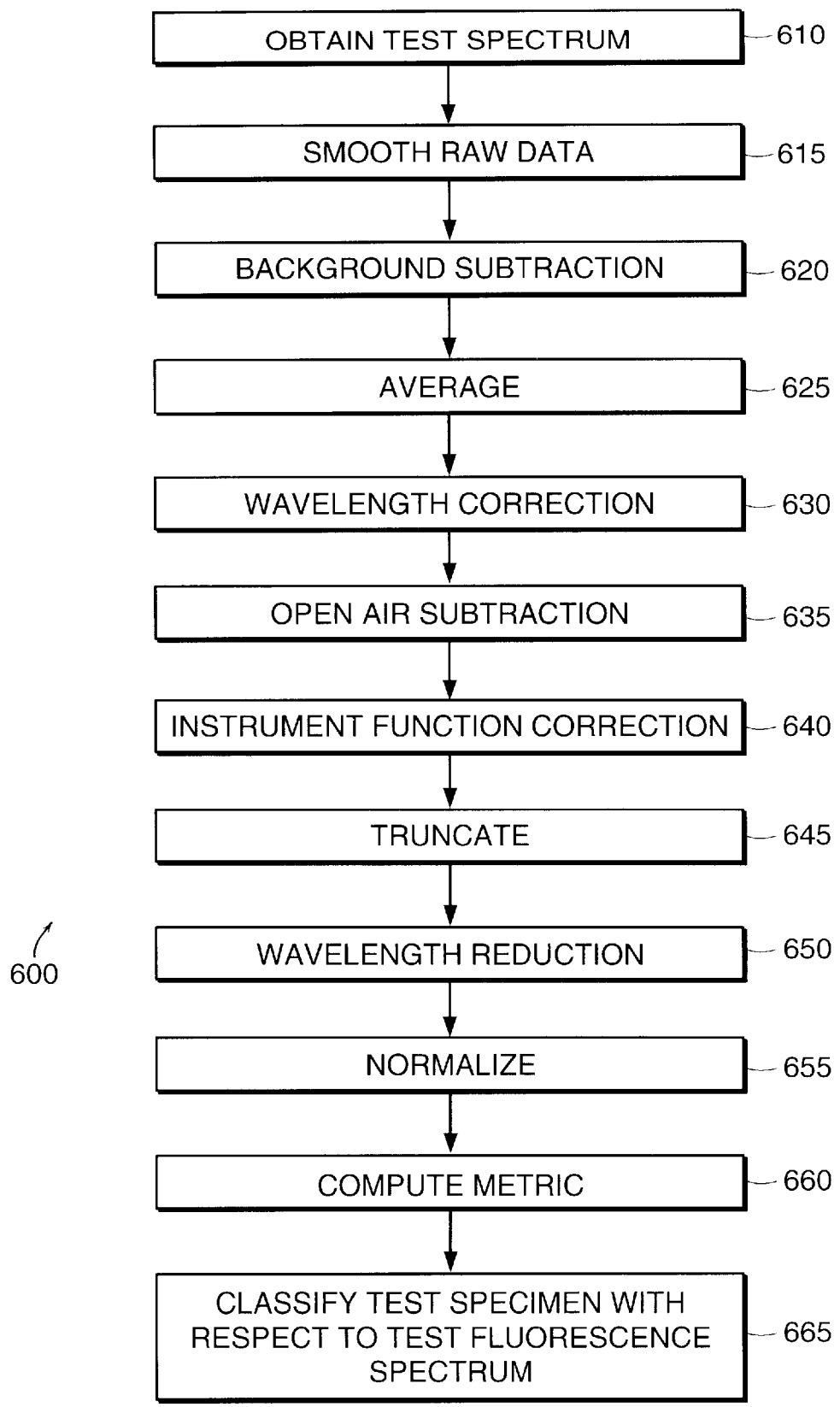
FIG. 6 is a schematic flow diagram depicting an analysis of a fluorescence spectrum in a system according to an illustrative embodiment of the invention.

FIG. 6 is a schematic flow diagram 600 depicting an analysis of a fluorescence spectrum in a system according to an illustrative embodiment of the invention. Fluorescence spectra such as the exemplary spectrum of FIG. 4 are suitable for the analysis described hereafter. The spectral analysis involves the measurement of spectra from a test specimen whose condition is to be determined, and employs a plurality of reference spectra taken from one or more specimens having known conditions. Those of ordinary skill in the spectroscopic arts will understand that the reference spectra can be obtained before, after, or at the same operation session as the test spectrum or spectra are obtained. For purposes of exposition, the treatment of the reference spectra will be described first. The treatment of a test spectrum will then be described.

In the present application, the term "characteristic N-dimensional value" should be understood to comprehend whichever of a point, a volume, a surface, a probability distribution or the like is used in the subsequent analysis. In mathematical terms, the "characteristic N-dimensional value" can be understood to be an ordered N-tuple of values, each one of which values can be expressed in its own dimensional units. It is well known in the spectroscopic arts to record one or more reference spectra from specimens that are known to have specific conditions. For example, it is known to record reference spectra from specimens having known states of health or known disease conditions. Reference spectra can be manipulated using the same pre-processing methods that are applied to spectra recorded from test specimens, so as to be able to compare spectra having substantially similar processing histories.

The computer 202 can store in a machine-readable memory for later use the information comprising the various characteristic N-dimensional values that are computed, as well as the corresponding known condition. The computer 202 can also similarly store in a machine-readable memory the various reference reflectance spectra data that were obtained.

Turning to the discussion of the recording and analysis of a test spectrum, as indicated in FIG. 6 at step 610, an operator collects and records a test fluorescence spectrum or a plurality of test fluorescence spectra from a test specimen of unknown state of health or unknown condition.

Step 615 indicates that the computer 202 can smooth the raw data. Various mathematical smoothing techniques are known in the art, such as computing moving averages, or applying filters to remove noise, for example using well-known convolution methods.

Step 620 indicates that the computer 202 can subtract a background reading, for example a reading taken using the systems and methods of FIGS. 1–3 with a standard specimen, or taken without a test specimen, from the reading observed from a test specimen or a reference specimen. In step 625, the computer 202 can average a plurality of spectral data taken from the same specimen, for example, the computer 202 can average N repeated spectral measurements taken from the same location of a single specimen, where N is an integer greater than 1.

In step 630, the computer 202 can correct the wavelength assigned to a particular amplitude of a spectrum, or can correct a plurality of such wavelengths. The computer 202 can perform such a correction by using a pre-recorded calibration file recorded from an optical source having lines at known wavelengths, for example a spectrum recorded from a lamp having the characteristic emission lines of mercury, or another well known emission source. The computer 202 uses the known wavelengths of the characteristic emission lines to determine a relationship between wavelength and a data channel number assigned by the computer 202 and an A/D converter to the characteristic spectra. The computer 202 can determine a wavelength for each A/D channel and thus knows the correct wavelength to assign to each amplitude.

As indicated in step 635, the computer 202 can correct the spectral data for effects ascribable to open air, such as absorption due to atmospheric constituents, for example gases such as water vapor, carbon dioxide, and others that have strong absorption at characteristic wavelengths.

Step 640 indicates that the computer 202 can correct for instrument-induced features by dividing an observed spectrum by an instrument function. The instrument function is obtained by dividing a known, accurate spectrum, such as a NIST-traceable tungsten lamp spectrum, by the observed spectrum recorded for illumination from such a lamp passing through the instrument of FIGS. 1 and 2. Dividing a first spectrum by a second spectrum involves dividing the respective amplitudes of the first spectrum by the corresponding amplitudes for the second spectrum and recording the result of each such division in a file as a function of the respective wavelengths, such as the instrument function.

Step 645 indicates that the computer 202 can truncate a spectrum to limit the data saved to a file as amplitudes corresponding to the reduced set of wavelengths, rather than all the wavelengths that the spectral instrument of FIGS. 1–2 is capable of recording. The truncation is performed to avoid saving data that has no significance, such as data corresponding to amplitudes having zero intensity for wavelengths beyond some predetermined value. In some embodiments, the operator can use the keyboard 206, or another input mechanism, to indicate one or both wavelength limits of the truncated wavelength range to be retained.

As indicated at step 650, the computer 202 can reduce the number of amplitudes, each amplitude corresponding to a selected wavelength, that are used to characterize a spectrum. In some embodiments, the number of amplitudes used to characterize a spectrum is fifty (50). In principle, as few as three amplitudes at three wavelengths may be sufficient to characterize a fluorescence spectrum as representing a test specimen comprising healthy normal squamous cells as distinguished from other tissue types having other states of health.

As indicated at step 655, the computer 202 can normalize the reduced spectral data using a system and method called normalization using non-uniform segmentation. Normalization using non-uniform segment normalization is described in detail in the co-pending patent application entitled "System for Normalizing Spectra," which application is commonly assigned to the assignee of the present application, and which application is incorporated herein by reference in its entirety.

In one embodiment, where the metric to be used in classifying a test specimen is a Mahalanaobis distance, the computer 202 performs a mathematical procedure intended to guarantee that a matrix used in further analytical steps is capable of being inverted. Matrix inversion is a mathematical process well known in the matrix mathematical arts. In one embodiment, the matrix that is computed is called a Friedman matrix. The data used in the calculation of the Friedman matrix is obtained from reference data recorded and stored in machine-readable format. The step of computing the appropriate Friedman matrix can be performed at any time after the reference spectral data is available.

Computation of the Mahalanobis distance requires the inversion of a weighting matrix. One approach (i.e., Linear Discriminant Analysis) utilizes the inverse of the pooled within-groups covariance while another method (Quadratic Discriminant Analysis) employs the inverse of each within-group covariance. When a "large" number of wavelengths are used (e.g., for large p), either of the aforementioned matrices can be singular and hence cannot be inverted. Therefore, an alternate weighting matrix called the Friedman matrix is used.

γ

The Friedman matrix is the weighted linear combination of a within-group covariance matrix $C_j$ and the pooled within-group covariance C that is a function of the Friedman parameters γ and λ. These parameters are selected from the unit interval [0,1]. It is important to note that the Friedman parameters are not physical quantities whose values carry classification information. Rather, they are used to insure that the weighting (Friedman) matrix is non-singular. Equation 1 details the p-by-p Friedman matrix, which is denoted by 'Ω.

$$\Omega_j(\gamma, \lambda) = \qquad \qquad \text{Eqn. 1}$$
$$(1-\gamma) \cdot [(1-\lambda) \cdot C_j + \lambda \cdot C] + \frac{\gamma}{p} \cdot tr[(1-\lambda) \cdot C_j + \lambda \cdot C] \cdot I_{p \times p}$$

N note that tr(A) is the trace of the matrix A, namely the sum of the diagonal elements. Also, $I_{p \times p}$ is the p-dimensional identity matrix.

$$A = \begin{bmatrix} a_{1,1} & a_{1,2} & \cdots & a_{1,n} \\ a_{2,1} & a_{2,2} & \cdots & a_{2,n} \\ \vdots & \vdots & \cdots & \vdots \\ a_{n,1} & a_{n,2} & \cdots & a_{n,n} \end{bmatrix} \Rightarrow tr(A) = \sum_{k=1}^{n} a_{k,k} \qquad \text{Eqn. 2}$$

$$I_{p \times p} = \begin{bmatrix} 1 & 0 & \cdots & 0 \\ 0 & 1 & \cdots & 0 \\ \vdots & \vdots & \cdots & \vdots \\ 0 & 0 & \cdots & 1 \end{bmatrix}_{p \times p} \qquad \text{Eqn. 3}$$

Let $s(\Lambda_p)$ be a p-dimensional spectrum. The Mahalanobis distance d from $s(\Lambda_p)$ to the group mean $\mu_j$ with respect to the associated Friedman matrix $'\Omega_j(\gamma, \lambda)$ and Friedman parameters γ and λ is given in equation 4 below.

$$d(s(\Lambda_p), \mu_j) = \sqrt{|(s(\Lambda_p) - \mu_j) \cdot \Omega_j(\gamma, \lambda)^{-1} \cdot (s(\Lambda_p) - \mu_j)^T|} \qquad \text{Eqn. 4}$$

Where other metrics are used to classify a test spectrum and a test specimen, the step 670 can be replaced by the appropriate computation.

As indicated at step 660, the computer 202 computes a metric from each test spectrum (or from an average value representing a plurality of spectra, such as performed at step 625) to each characteristic N-dimensional value for the reference spectra recorded. In one embodiment, the metric can be a Mahalanobis distance, as indicated above. In other embodiments, the metric can be the square root of the sum of the squares of the differences in coordinates in the N-dimensional space, or the metric can be the Bhattacharyya distance.

At step 665, the computer 202 examines the results obtained in step 660, and determines a classification for the test specimen, based on the metrics computed with respect to the test fluorescence spectrum and a classification rule or relation. In one embodiment, the classification relation is that the condition of the test specimen is assigned as the condition corresponding to the reference spectrum constellation or set having the Mahalanobis shortest distance, provided that the shortest Mahalanobis distance is less than a pre-determined minimum distance. In one embodiment, if no Mahalanobis distance is less than a pre-determined minimum distance, the test spectrum is discarded as being incapable of being classified, or indeterminate.

In one embodiment, the test fluorescence spectrum can be compared to multiple sets of reference spectra in a single comparison. In one embodiment, the computations can be repeated for different sets of reference conditions. For example, a test fluorescence spectrum from a test specimen can be compared in a first computation to reference fluorescence spectral data for normal squamous tissue and CIN II/III tissue, compared in a second computation to reference fluorescence spectral data for normal squamous tissue and CIN I tissue, and compared in a third computation to reference fluorescence spectral data for normal squamous tissue and metaplasia tissue. If the test fluorescence spectrum is classified in each of the three comparisons as being more closely related to the reference spectra for normal squamous tissue, the test specimen can be classified by the computer 202 as having normal health, and the classification process is complete. However, if the test fluorescence spectrum is classified in either of the comparisons involving CIN I or CIN II/III as being less closely related to the reference spectra for normal squamous tissue than one of the other conditions or states of health (namely CIN I, or CIN II/III), the computer 202 can report that the state of health of the test specimen is not clearly that of normal squamous tissue, and that further analysis is in order. In one embodiment, the further analysis involves the recording and examination of reflectance spectra.

Figure 7:
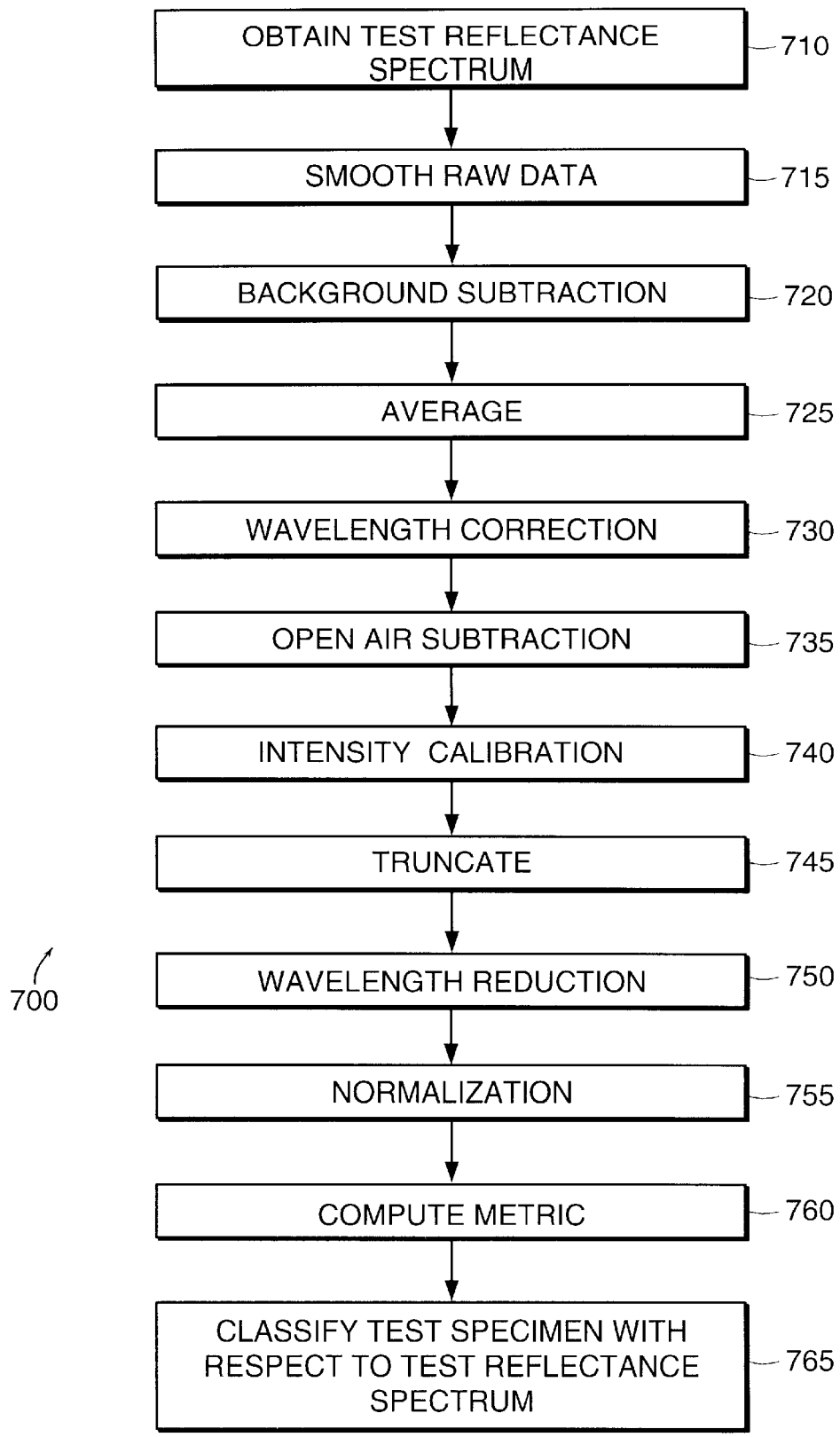
FIG. 7 is a schematic flow diagram depicting an analysis of a reflectance spectrum in a system according to an illustrative embodiment of the invention.

FIG. 7 is a schematic flow diagram 700 depicting an analysis of a reflectance spectrum in a system according to an illustrative embodiment of the invention. Reflectance spectra such as the exemplary spectrum of FIG. 5 are suitable for the analysis described hereafter. The spectral analysis involves the measurement of spectra from a test specimen whose condition is to be determined, and employs a plurality of reference spectra taken from one or more specimens having known conditions. Those of ordinary skill in the spectroscopic arts will understand that the reference spectra can be obtained before, after, or at the same operation session as the test spectrum or spectra are obtained.

The computer 202 can store in a machine-readable memory for later use the information comprising the various characteristic N-dimensional values that are computed, as well as the corresponding known condition. The computer 202 can also similarly store in a machine-readable memory the various reference reflectance spectra data that were obtained.

Turning to the discussion of the recording an analysis of a test spectrum, as indicated in FIG. 7 at step 710, an operator collects and records a test reflectance spectrum or a plurality of test reflectance spectra from a test specimen of unknown state of health or unknown condition.

Step 715 indicates that the computer 202 can smooth the raw data. Various mathematical smoothing techniques are known in the art, such as computing moving averages, or applying filters to remove noise, for example using well-known convolution methods.

Step 720 indicates that the computer 202 can subtract a background reading, for example a reading taken using the systems and methods of FIGS. 1–3 with a standard specimen, or taken without a test specimen, from the reading observed from a test specimen or a reference specimen. In step 725, the computer 202 can average a plurality of spectral data taken from the same specimen, for example, the computer 202 can average N repeated spectral measurements taken from the same location of a single specimen, where N is an integer greater than 1.

In step 730, the computer 202 can correct the wavelength assigned to a particular amplitude of a spectrum, or can correct a plurality of such wavelengths. The computer 202 can perform such a correction by using a pre-recorded calibration file recorded from an optical source having lines at known wavelengths, for example a spectrum recorded from a lamp having the characteristic emission lines of mercury, or another well known emission source. The computer 202 uses the known wavelengths of the characteristic emission lines to determine a relationship between wavelength and a data channel number assigned by the computer 202 and an A/D converter to the characteristic spectra. The computer 202 can determine a wavelength for each A/D channel and thus knows the correct wavelength to assign to each amplitude.

As indicated in step 735, the computer 202 can correct the spectral data for effects ascribable to open air, such as absorption due to atmospheric constituents, for example gases such as water vapor, carbon dioxide, and others that have strong absorption at characteristic wavelengths.

Step 740 indicates that the computer 202 can correct for instrument-induced features by dividing an observed spectrum by an instrument function. The instrument function is obtained by dividing a known, accurate spectrum, such as a NIST-raceable tungsten lamp spectrum, by the observed spectrum recorded for illumination from such a lamp passing through the instrument of FIGS. 1 and 2. Dividing a first spectrum by a second spectrum involves dividing the respective amplitudes of the first spectrum by the corresponding amplitudes for the second spectrum and recording the result of each such division in a file as a function of the respective wavelengths, such as the instrument function.

Step 745 indicates that the computer 202 can truncate a spectrum to limit the data saved to a file as amplitudes corresponding to the reduced set of wavelengths, rather than all the wavelengths that the spectral instrument of FIGS. 1–2 is capable of recording. The truncation is performed to avoid saving data that has no significance, such as data corresponding to amplitudes having zero intensity for wavelengths beyond some predetermined value. In some embodiments, the operator can use the keyboard 206, or another input mechanism, to indicate one or both wavelength limits of the truncated wavelength range to be retained.

As indicated at step 750, the computer 202 can reduce the number of amplitudes, each amplitude corresponding to a selected wavelength, that are used to characterize a spectrum. In some embodiments, the number of amplitudes used to characterize a spectrum is fifty (50). In principle, as few as three amplitudes at three wavelengths may be sufficient to characterize a reflectance spectrum as representing a test specimen comprising healthy normal squamous cells as distinguished from other tissue types having other states of health.

As indicated at step 755, the computer 202 can normalize the reduced spectral data using a system and method called mean normalization. Mean normalization involves determining a mean value at each wavelength of interest for reference reflectance spectra and subtracting the mean values so determined at a particular wavelength of interest from the amplitude of the test spectrum (or spectra) at the same wavelength.

In one embodiment, at step 760, where the metric to be used in classifying a test specimen is a Mahalanaobis distance, the computer 202 performs a mathematical procedure intended to guarantee that a matrix used in further analytical steps is capable of being inverted. Matrix inversion is a mathematical process well known in the matrix mathematical arts. In one embodiment, the matrix that is computed is called a Friedman matrix. The data used in the calculation of the Friedman matrix is obtained from the stored data recorded in machine-readable format. The step of computing the appropriate Friedman matrix can be performed at any time after the reference spectral data is available.

Computation of the Mahalanobis distance requires the inversion of a weighting matrix. One approach (i.e., Linear Discriminant Analysis) utilizes the inverse of the pooled within-groups covariance while another method (Quadratic Discriminant Analysis) employs the inverse of each within-group covariance. When a "large" number of wavelengths are used (e.g., for large p), either of the aforementioned matrices can be singular and hence cannot be inverted. Therefore, an alternate weighting matrix called the Friedman matrix is used.

The Friedman matrix is the weighted linear combination of a within-group covariance matrix $C_j$ and the pooled within-group covariance C that is a function of the Friedman parameters $\gamma$ and $\lambda$. These parameters are selected from the unit interval [0,1]. It is important to note that the Friedman parameters are not physical quantities whose values carry classification information. Rather, they are used to insure that the weighting (Friedman) matrix is non-singular. Equation 5 details the p-by-p Friedman matrix, which is denoted by $'\Omega$.

$$\Omega_j(\gamma, \lambda) = \qquad \text{Eqn. 5}$$

$$(1-\gamma) \cdot [(1-\lambda) \cdot C_j + \lambda \cdot C] + \frac{\gamma}{p} \cdot tr[(1-\lambda) \cdot C_j + \lambda \cdot C] \cdot I_{p \times p}$$

N note that tr(A) is the trace of the matrix A, namely the sum of the diagonal elements. Also, $I_{p \times p}$ is the p-dimensional identity matrix.

$$A = \begin{bmatrix} a_{1,1} & a_{1,2} & \cdots & a_{1,n} \\ a_{2,1} & a_{2,2} & \cdots & a_{2,n} \\ \vdots & \vdots & \cdots & \vdots \\ a_{n,1} & a_{n,2} & \cdots & a_{n,n} \end{bmatrix} \Rightarrow tr(A) = \sum_{k=1}^{n} a_{k,k} \qquad \text{Eqn. 6}$$

$$I_{p \times p} = \begin{bmatrix} 1 & 0 & \cdots & 0 \\ 0 & 1 & \cdots & 0 \\ \vdots & \vdots & \cdots & \vdots \\ 0 & 0 & \cdots & 1 \end{bmatrix}_{p \times p} \qquad \text{Eqn. 7}$$

Let $s(\Lambda_p)$ be a p-dimensional spectrum. The Mahalanobis distance d from $s(\cdot_p)$ to the group mean $\mu_j$ with respect to the associated Friedman matrix $'\Omega(\gamma, \lambda)$ and Friedman parameters $\gamma$ and $\lambda$ is given in equation 8 below.

$$d(s(\Lambda_p), \mu_j) = \sqrt{|(s(\Lambda_p) - \mu_j) \cdot \Omega_j(\gamma, \lambda)^{-1} \cdot (s(\Lambda_p) - \mu_j)^T|} \qquad \text{Eqn. 8}$$

Where other metrics are used to classify a test spectrum and a test specimen, the step 770 can be replaced by the appropriate computation.

As indicated at step 760, the computer 202 computes a metric from each test spectrum (or from an average value representing a plurality of spectra, such as performed at step 725) to each characteristic N-dimensional value for the reference spectra recorded. In one embodiment, the metric can be a Mahalanobis distance, as indicated above. In other embodiments, the metric can be the square root of the sum of the squares of the differences in coordinates in the N-dimensional space, or the metric can be the Bhattacharyya distance.

At step 765, the computer 202 examines the results obtained in step 760, and determines a classification for the test specimen, based on the metrics computed with respect to the test reflectance spectrum and a classification rule or relation. In one embodiment, the classification relation is that the condition of the test specimen is assigned as the condition corresponding to the reference spectrum constellation or set having the Mahalanobis shortest distance, provided that the shortest Mahalanobis distance is less than a pre-determined minimum distance. In one embodiment, if no Mahalanobis distance is less than a pre-determined minimum distance, the test spectrum is discarded as being incapable of being classified, or indeterminate.

In one embodiment, the test reflectance spectrum can be compared to multiple sets of reference spectra in a single comparison. In one embodiment, the computations can be repeated for different sets of reference conditions. For example, a test reflectance spectrum from a test specimen can be compared in a first computation to reference reflectance spectral data for normal squamous tissue and CIN II/III tissue, compared in a second computation to reference reflectance spectral data for normal squamous tissue and CIN I tissue, and compared in a third computation to reference reflectance spectral data for normal squamous tissue and metaplasia tissue. If the test reflectance spectrum is classified in each of the three comparisons as being more closely related to the reference spectra for normal squamous tissue, the test specimen can be classified by the computer 202 as having normal health, and the classification process is complete. However, if the test reflectance spectrum is classified in either of the comparisons involving CIN I or CIN II/III as being less closely related to the reference spectra for normal squamous tissue than one of the other conditions or states of health (namely CIN I, or CIN II/III), the computer 202 can report that the state of health of the test specimen is not clearly that of normal squamous tissue, and that further analysis is in order. In one embodiment, the further analysis involves the recording and examination of reflectance spectra.

Equivalents

While the invention has been particularly shown and described with reference to specific preferred embodiments, it should be understood by those skilled in the art that various changes in form and detail may be made therein without departing from the spirit and scope of the invention as defined by the appended claims:

What is claimed is:

1. A method of determining a condition of a test specimen, said method comprising,
   identifying a plurality of first test specimens having a first known condition and observing from each of said first test specimens a first fluorescence spectrum characteristic of said first known condition,
   obtaining an average reflectance spectrum from said plurality of first test specimens,
   obtaining a reflectance spectrum from a second test specimen that is observed to produce a second fluorescence spectrum that is not characteristic of said first known condition,
   obtaining a reflectance spectrum residual by subtracting said average reflectance spectrum from said reflectance spectrum obtained from said second test specimen, and
   determining said condition of said second test specimen based at least in part on an amplitude of one or more features of said reflectance spectrum residual.

2. The method of claim 1, wherein said plurality of first test specimens comprise a plurality of first tissue specimens and said second test specimen comprises a second tissue specimen.

3. The method of claim 2, wherein said plurality of first tissue specimens and said second test specimen comprise human cervical tissue, said first known condition is a known state of health, and said condition of said second test specimen is a state of health to be determined.

4. The method of claim 2, wherein said known state of health comprises one of the conditions of normal squamous tissue, metaplasia, CIN I, and CIN II/III.

5. The method of claim 1, further comprising,
   obtaining additional optical information from said second test specimen, and
   evaluating said additional optical information with said fluorescence spectrum and said reflectance spectrum from said second test specimen to determine said condition of said second test specimen.

6. The method of claim 5, wherein said additional optical information comprises video information.

7. The method of claim 5, wherein said additional optical information comprises an optical image.

8. The method of claim 5, wherein said plurality of first test specimens comprise a plurality of first tissue specimens and said second test specimen comprises a second tissue specimen.

9. The method of claim 8, wherein said plurality of first tissue specimens and said second tissue specimen comprise human cervical tissue, said first known condition is a known state of health, and said condition of said second test specimen is a state of health to be determined.

10. The method of claim 8, wherein said known state of health comprises one of the conditions of normal squamous tissue, metaplasia, CIN I, and CIN II/III.

11. A spectroscopic system for determining a condition of a test specimen, comprising,
- a data collection module that observes a first fluorescence spectrum characteristic of a first known condition from each of a plurality of first test specimens having said first known condition, that observes a first reflectance spectrum from each of said plurality of first test specimens, and that observes a reflectance spectrum from a second test specimen that is observed to produce a second fluorescence spectrum that is not characteristic of said first known condition,
- a computation module that compute an average reflectance spectrum from said first reflectance spectrum from each of said plurality of first test specimens, and that computes a reflectance spectrum residual by subtracting said average reflectance spectrum from said reflectance spectrum obtained from said plurality of second test specimens, and
- an analysis module that determines a condition of said second test specimen based at least in part on an amplitude of one or more features of said reflectance spectrum residual.

12. The system of claim 11, wherein said plurality of first test specimens comprise a plurality of first tissue specimens and said second test specimen comprises a second tissue specimen.

13. The system of claim 12, wherein said plurality of first tissue specimens and said second tissue specimen comprise human cervical tissue, said first known condition is a known state of health, and said condition of said second test specimen is a state of health to be determined.

14. The system of claim 12, wherein said known state of health comprises one of the conditions of normal squamous tissue, metaplasia, CIN I, and CIN II/III.

15. The system of claim 11, wherein said data collection module obtains additional optical information from said second test specimen, and
- said analysis module evaluates said additional optical information with said fluorescence spectrum and said reflectance spectrum from said second test specimen to determine said condition of said second test specimen.

16. The system of claim 15, wherein said additional optical information comprises video information.

17. The system of claim 15, wherein said additional optical information comprises an optical image.

18. The system of claim 15, wherein said plurality of first test specimens comprise a plurality of first tissue specimens and said second test specimen comprises a second tissue specimen.

19. The system of claim 18, wherein said plurality of first tissue specimens and said second tissue specimen comprise human cervical tissue, said first known condition is a known state of health, and said condition of said second test specimen is a state of health to be determined.

20. The system of claim 18, wherein said known state of health comprises one of the conditions of normal squamous tissue, metaplasia, CIN I, and CIN II/III.

21. A method of determining a disease state in a specimen, the method comprising the steps of:
- obtaining a reflectance spectrum from a test specimen having a fluorescence spectrum that is not characteristic of a healthy tissue;
- subtracting an average reflectance spectrum obtained from a plurality of specimens from said reflectance spectrum to produce a reflectance spectrum residual, each producing a fluorescence spectrum characteristic of healthy tissue; and
- determining disease state in said test specimen based upon one or more characteristics of said reflectance spectrum residual.

22. The method of claim 21, wherein said test specimen is selected from the group consisting of cervical tissue, intestinal tissue, esophageal tissue, and skin tissue.

23. The method of claim 21, wherein said disease state is selected from the group consisting of normal squamous tissue, metaplasia, CIN I, and CIN II/III.

* * * * *